United States Patent
Chelak

(10) Patent No.: US 7,981,094 B2
(45) Date of Patent: Jul. 19, 2011

(54) TWO POSITION SEPTUM FOR IMPLANTABLE VASCULAR ACCESS DEVICE

(75) Inventor: Todd M. Chelak, Westborough, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/211,866

(22) Filed: Sep. 17, 2008

(65) Prior Publication Data

US 2009/0088704 A1   Apr. 2, 2009

Related U.S. Application Data

(60) Provisional application No. 60/995,749, filed on Sep. 28, 2007.

(51) Int. Cl.
A61M 31/00 (2006.01)
A61M 29/00 (2006.01)

(52) U.S. Cl. ............................. 604/288.01; 604/96.01

(58) Field of Classification Search . 604/288.01–288.04, 93.01, 165.04–167.04, 604/167.06, 171, 174–175, 201–206, 533–538; 606/108

See application file for complete search history.

(56) References Cited

U.S. PATENT DOCUMENTS

| | | | |
|---|---|---|---|
| 5,318,545 A | 6/1994 | Tucker | |
| 5,514,133 A * | 5/1996 | Golub et al. | 606/1 |
| 5,562,617 A | 10/1996 | Finch, Jr. et al. | |
| 5,713,859 A | 2/1998 | Finch, Jr. et al. | |
| 5,755,780 A | 5/1998 | Finch, Jr. et al. | |
| 5,792,123 A | 8/1998 | Ensminger | |
| 6,319,226 B1 | 11/2001 | Sherry | |
| 6,540,717 B2 | 4/2003 | Sherry | |
| 6,855,129 B2 * | 2/2005 | Jensen et al. | 604/110 |
| 7,252,649 B2 | 8/2007 | Sherry | |
| 7,867,221 B2 * | 1/2011 | Haase | 604/891.1 |
| 2005/0024175 A1 * | 2/2005 | Gray et al. | 335/220 |

* cited by examiner

Primary Examiner — Nicholas D Lucchesi
Assistant Examiner — Rebecca E Eisenberg
(74) Attorney, Agent, or Firm — Thomas M. Johnston, Esq.

(57) ABSTRACT

An implantable access device for intravenous delivery and/or withdrawal of fluids is described herein. The access device includes a septum which is movably supported within a housing of the access device from a retracted, low profile position to an extended, high profile position to facilitate easy identification of the location of the septum by medical personnel.

14 Claims, 10 Drawing Sheets

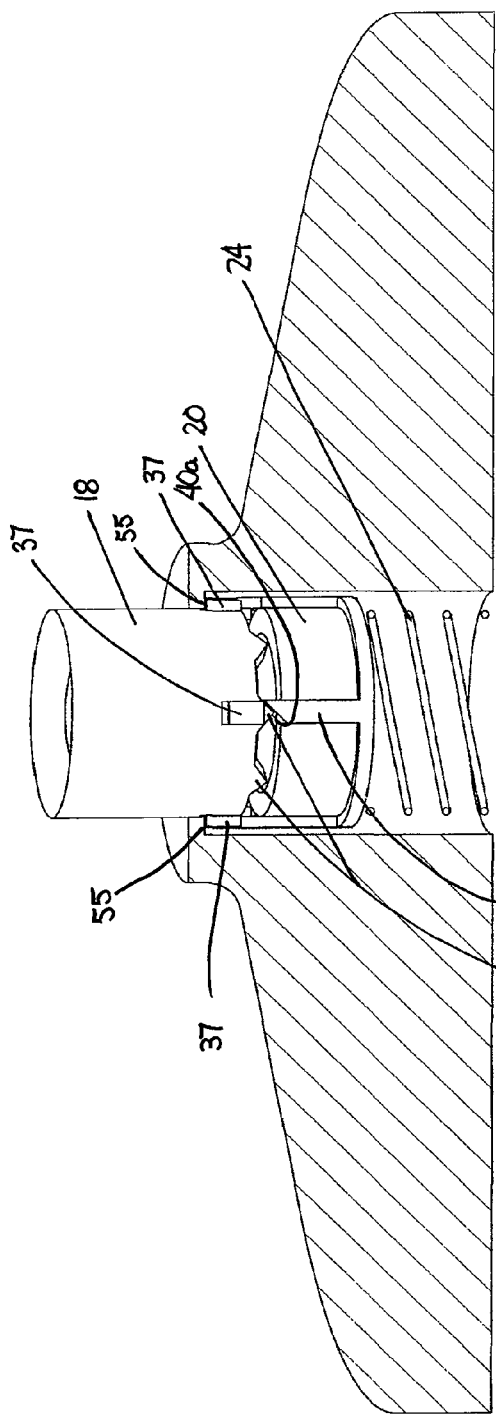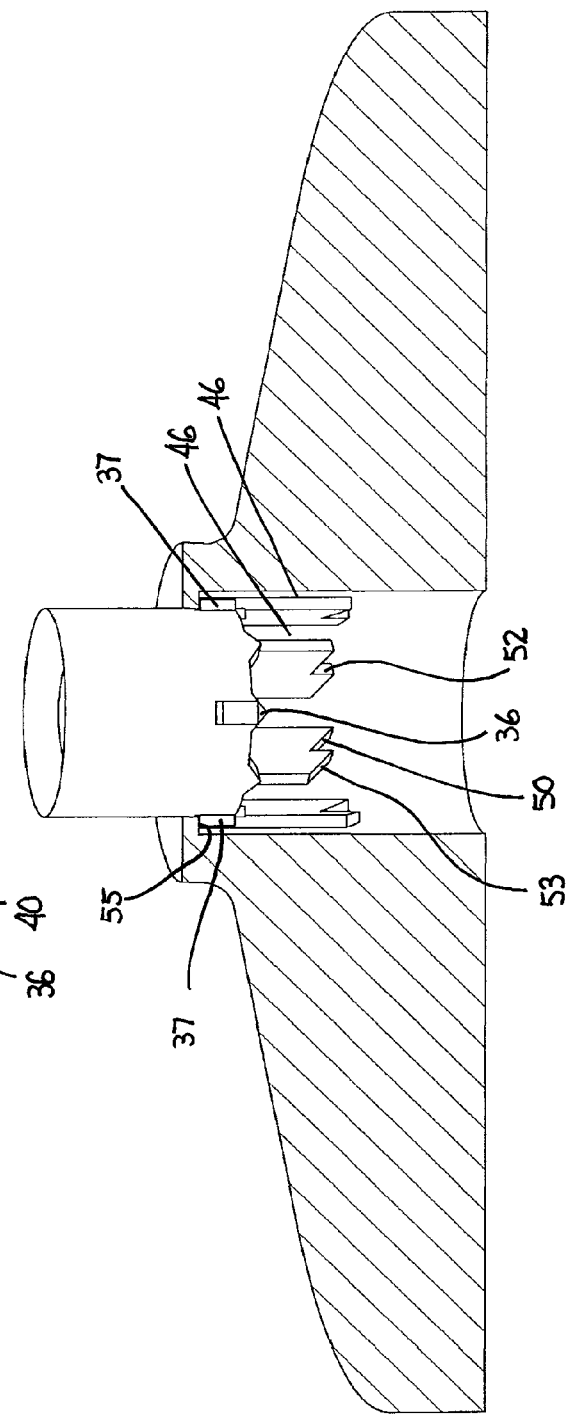

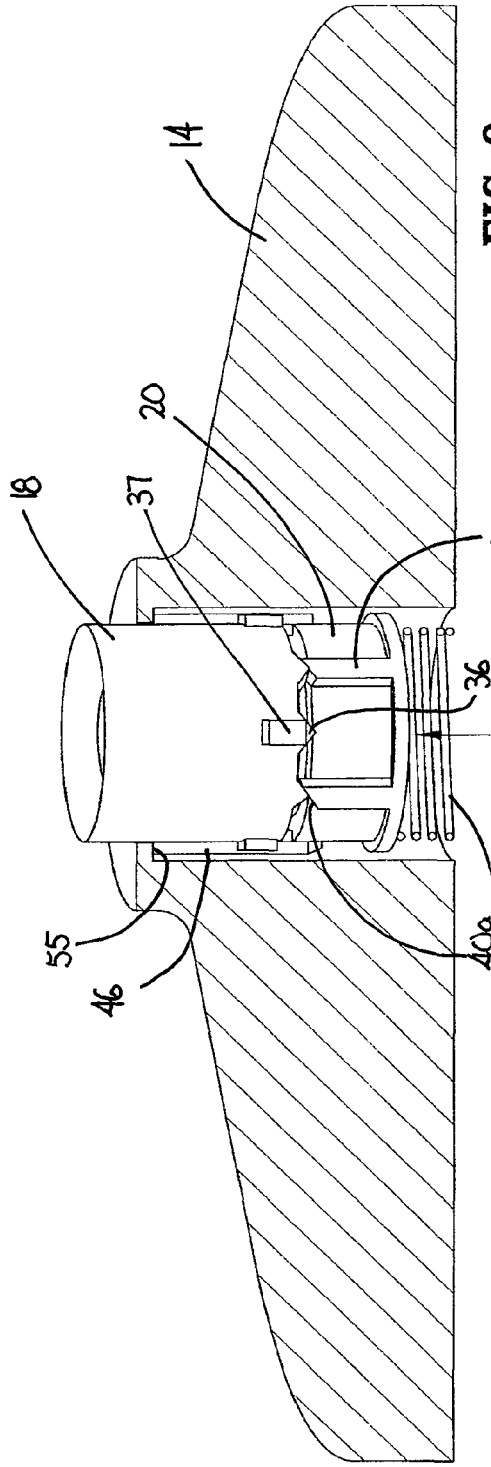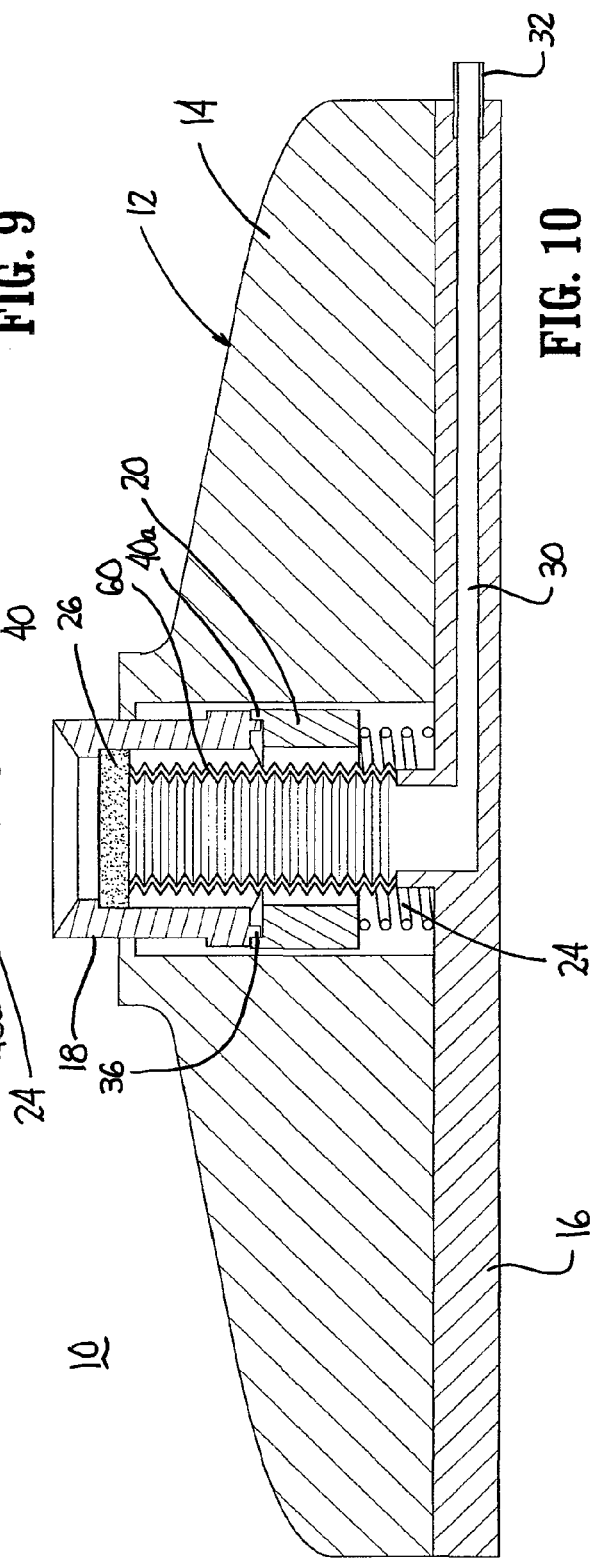

TWO POSITION SEPTUM FOR IMPLANTABLE VASCULAR ACCESS DEVICE

This application claims priority from U.S. Provisional Application Ser. No. 60/995,749, which was filed on Sep. 28, 2007 and is incorporated herein in its entirety by reference.

BACKGROUND

1. Technical Field

The present disclosure relates to implantable access devices for intravenous delivery and/or withdrawal of fluids. More particularly, the present disclosure relates to an implantable access device having a septum which can be moved to a high profile position to assist medical personnel in locating the septum.

2. Background of Related Art

Implantable access devices for intravenous fluid delivery and/or withdrawal are well known in the medical arts. Typically, such devices are implanted under the skin to allow for intermittent access to a selected vascular structure, such as an artery or vein. These devices are most commonly used in patients who require repeated injections on a daily basis and/or require repeated injections with large diameter needles, such as during hemodialysis procedures where relatively large needles and/or catheters in the range of 14 gauge or higher are required.

One problem associated with such access devices is that once the access device has been surgically implanted beneath the skin, the septum or pierceable membrane of the access device through which the injection occurs, is not visible. Thus, it may require one or more attempts by medical personnel to locate the septum of the access device.

Accordingly, a continuing need exists in the medical arts for an access device which includes a septum which can be easily identified by medical personnel prior to a medical procedure.

SUMMARY

An implantable access device is provided which includes a housing defining a cavity and an outlet channel, the cavity being in fluid communication with the outlet channel. A septum encloses an upper end of the cavity. The septum is movably supported in relation to the housing and is movable from a first, lower-profile position to a second, higher-profile position located externally of the cavity. The access device also includes an upper collar and a lower collar. The upper collar is positioned within the cavity and defines a throughbore. The septum is supported on the upper collar and seals one end of the throughbore of the upper collar. In one embodiment, the upper collar is movable within the cavity from a first position to a second position to move the septum from the lower-profile position to the higher-profile position. The lower collar is rotatably supported within the cavity of the housing.

In one embodiment, a biasing member is positioned to urge the upper collar from the first position to the second position. A lower end of the upper collar may be positioned within the cavity to abut an upper end of the lower collar. The lower end of the upper collar may include at least one angled protrusion and the upper end of the lower collar may include at least one rib such that the at least one angled protrusion engages the at least one rib to apply torque to the lower collar.

In one embodiment, the access device includes a cam assembly defining at least one retaining member and at least one channel. The rib of the lower collar and at least one guide rib of the upper collar are slidable within the at least one channel.

In one embodiment, the cam assembly is fixedly secured within the housing such that the upper collar and the lower collar are rotatably fixed within the housing when the rib of the lower collar and the guide rib of the upper collar are positioned within the at least one channel. When the upper collar is in the first position, the rib of the lower collar is pushed from the at least one channel and rotated by the angled protrusion, such that the rib engages the retaining member and the lower collar is retained in a lower portion of the cavity to retain the upper collar in the first position and retain the septum in the lower-profile position.

In one embodiment, the at least one retaining member includes an angled recess and a stop member. The rib engages the stop member when the septum is retained in the lower-profile position. When the septum is in the lower-profile position, the upper collar can be pressed downwardly to urge the lower collar downwardly within the cavity to disengage the at least one rib of the lower collar from the stop member and allow the lower collar to rotate to realign the at least one rib with the at least one channel such that the biasing member moves the septum to the higher-profile position.

The access device may include an annular sleeve having a first end connected to a bottom surface of the septum and a second end connected to the housing. The sleeve defines a sealed flow path between the septum and the outlet channel. The annular sleeve may be in the form of a bellows-like member.

BRIEF DESCRIPTION OF THE DRAWINGS

Various embodiments of the presently disclosed vascular access device and method of use are disclosed herein with reference to the drawings, wherein:

FIG. 4 is a perspective, partial cross-sectional view of the access device shown in FIG. 1 with the upper collar in an extended position and the septum and sleeve removed;

FIG. 5 is a perspective, partial cross-sectional view of the access device shown in FIG. 4 with the upper collar in an extended position and the lower collar, biasing member, sleeve and septum removed from the device;

FIG. 9 is a side, partial cross-sectional view of the access device shown in FIG. 7 as the lower collar moves into engagement with the retaining members;

FIG. 10 is a side, cross-sectional view of the access device shown in FIG. 7 with the septum in the retracted position;

DETAILED DESCRIPTION OF EMBODIMENTS

Figure 1:
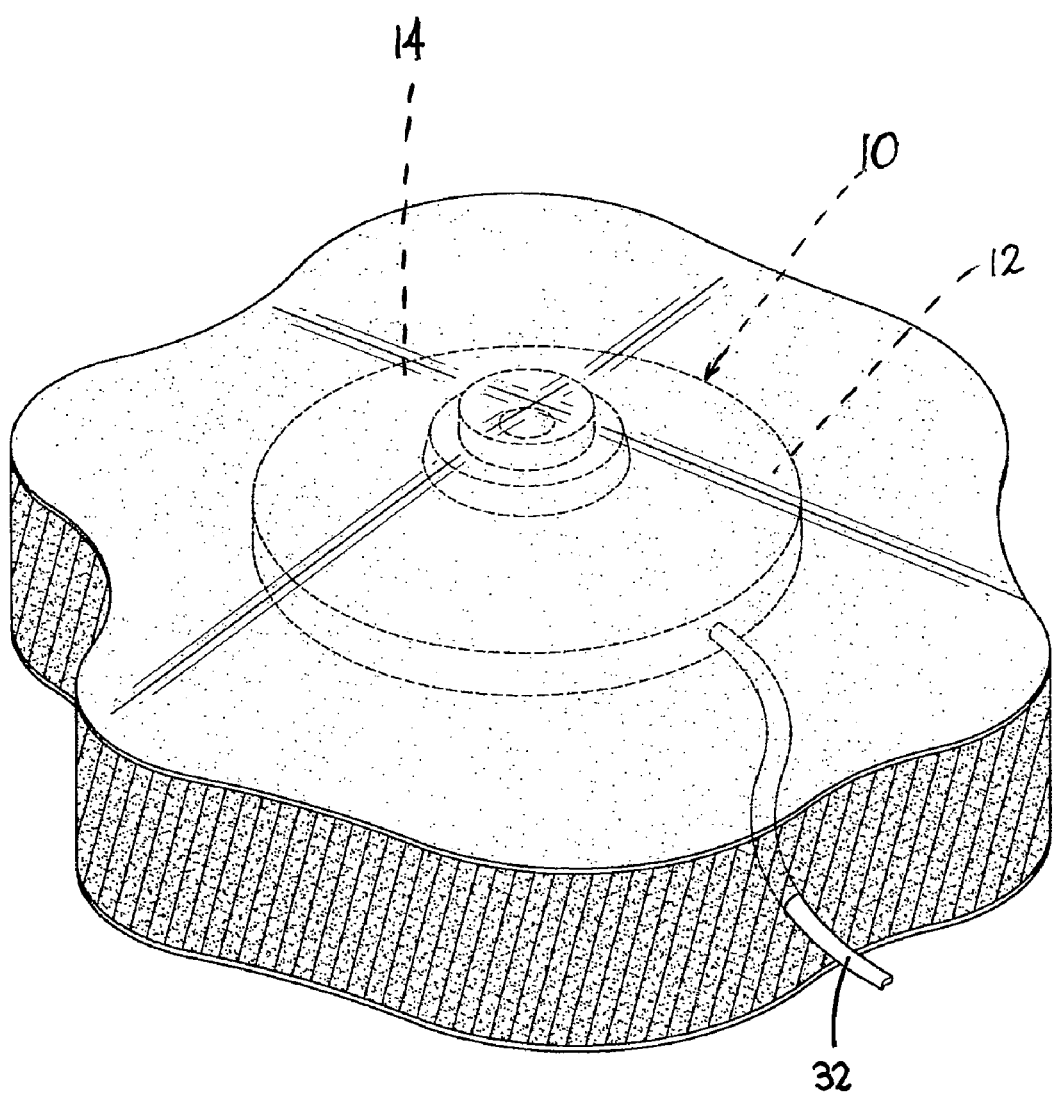
FIG. 1 is a side perspective cross-sectional view of one embodiment of the presently disclosed access device shown in phantom implanted in a patient with the septum in a retracted position.
Figure 2:
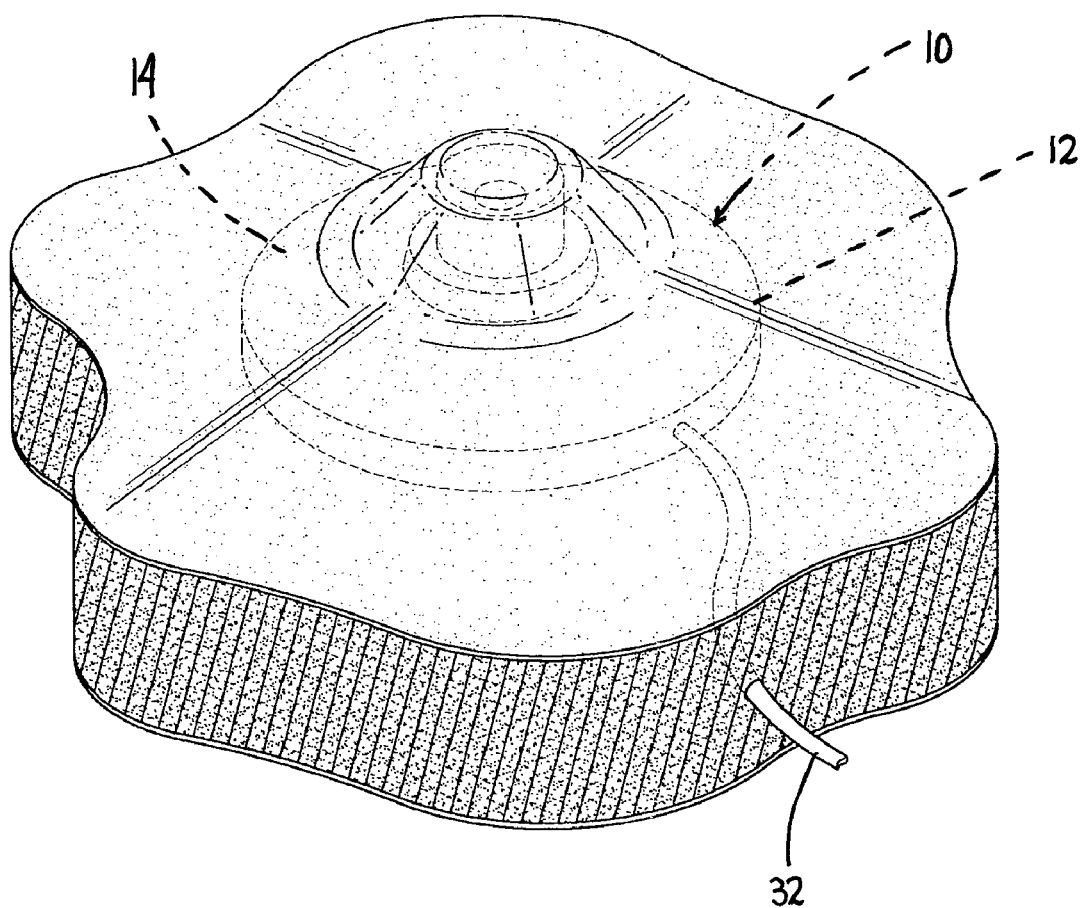
FIG. 2 is a side perspective cross-sectional view of the access device shown in FIG. 1 in phantom implanted in a patient with the septum in an extended position.

Embodiments of the presently disclosed implantable access device will now be described in detail with reference to the drawings wherein like reference numerals designate identical or corresponding elements in each of the several views.

FIGS. 1-6 illustrate one embodiment of the presently disclosed access device shown generally as 10. Access device 10 includes a housing 12 having an upper body portion 14, a lower body portion 16 (FIG. 6) an upper collar 18, a lower collar 20, a biasing member 24 and a septum 26. Upper body portion 14 of housing 12 defines a cavity 28 dimensioned to receive the various components of device 10 as will be described in further detail below. A cam assembly 22 is formed along the inner wall 15 of upper body portion 14 of housing 12. Lower body portion 16 defines an outlet channel 30 (FIG. 6) that fluidly communicates a bottom of cavity 28 with a catheter 32.

Referring to FIGS. 3-6, upper collar 18 has a substantially cylindrical body 34 which defines a throughbore 34a. Alternatively, it is envisioned that upper collar 18 may have a variety of different configurations. Septum 26 is supported in an upper end of throughbore 34a using any known fastening technique, e.g., adhesives, welding, press-fitting, etc. See FIG. 6. A proximal end of upper collar 18 includes a series of angled protrusions 36 and a plurality of guide ribs 37. Angled protrusions 36 can have a substantially triangular shape and are configured and dimensioned to interact with lower collar 20 to effect rotation of lower collar 20 within housing 12 as will be described in further detail below. Guide ribs 37 rotatably fix upper collar 18 within cavity 28 of housing 12 and define the uppermost or extended position of upper collar 18 as will also be described in further detail below.

Lower collar 20 is substantially cylindrical and defines a throughbore 38. A series of longitudinal ribs 40 are positioned about the external surface of collar 20. An upper end 40a of each of ribs 40 is positioned to engage angled projections 36 of upper collar 18 to effect rotation of lower collar 20 as will be described in detail below. Upper end 40a of ribs 40 may be tapered or angled.

Figure 3:
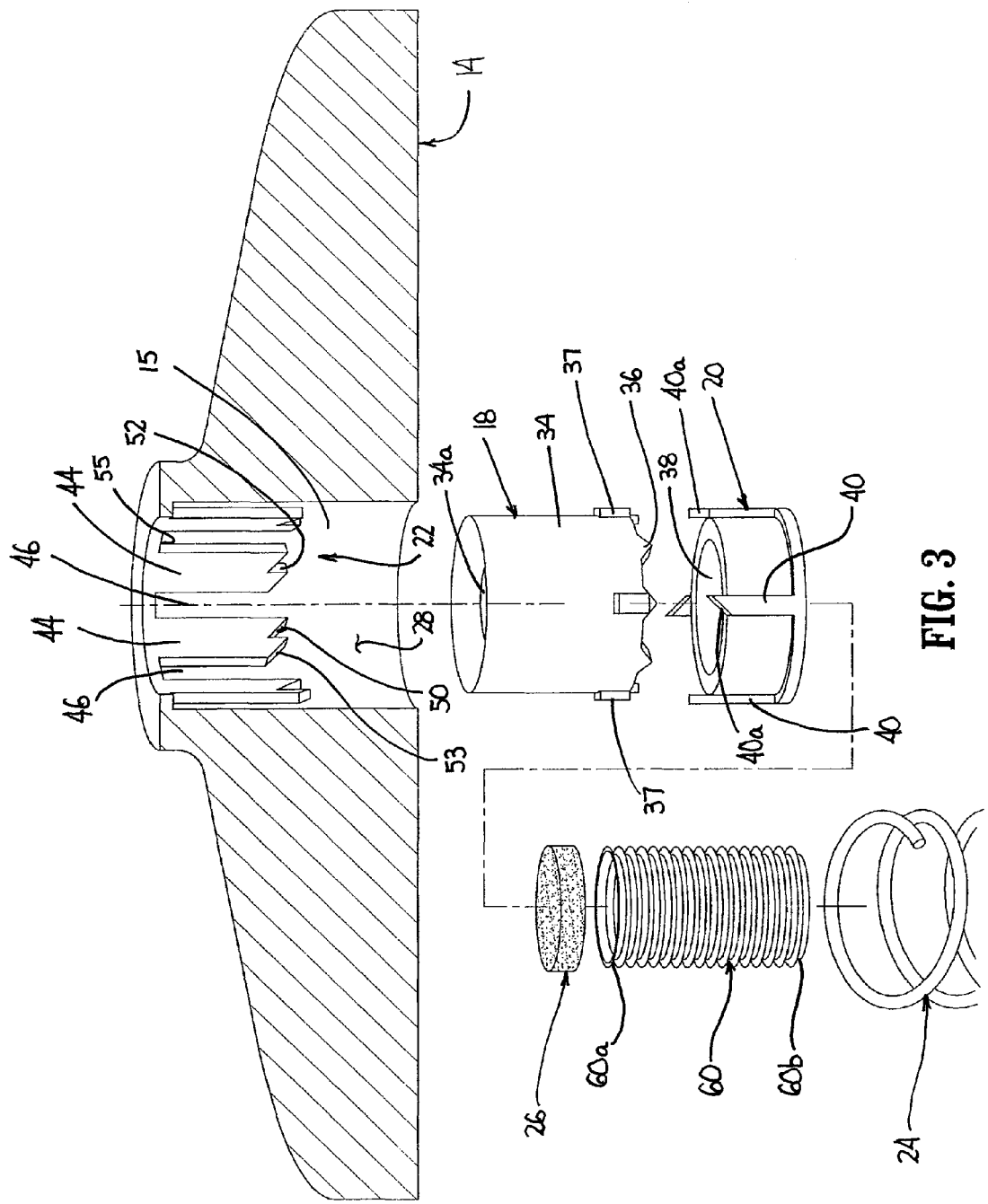
FIG. 3 is a perspective, partial cross-sectional, exploded view of the access device shown in FIG. 1.

Referring to FIGS. 3 and 5, cam assembly 22 includes a series of retaining members 44 positioned annularly about cavity 28 of upper body portion 14. Each of retaining members 44 is separated from adjacent retaining members 44 by channels 46. Each retaining member 44 includes a lower end which defines an angled, recessed surface 50, a vertical stop portion 52 and an angled or sloped guide surface 53. In an alternative embodiment, the cam assembly may be provided on an annular cam member 22 which is separate from housing 12 and is fixedly positioned within housing 12 and dimensioned to be positioned about a lower end of upper collar 18 and lower collar 20. When upper collar 18 and lower collar 20 are assembled within cavity 28 of upper body portion 14 of housing 12, guide ribs 37 of upper collar 18 and longitudinal ribs 40 of lower collar 20 are slidably positioned within channels 46 of cam assembly 22. As illustrated in FIG. 3, an upper end of each of channels 46 is closed and defines an abutment surface 55 which engages guide ribs 37 to define the extended position of upper collar 18 and prevent separation of collar 18 from housing 12.

Referring to FIGS. 3-6, biasing member 24, which may be a coil spring, is positioned within cavity 28 between lower body portion 16 (FIG. 6) and a lower end of lower collar 20 such that lower collar 20 is urged upwardly towards upper collar 18. When ribs 40 of lower collar 20 are aligned with channels 46 of cam assembly 22, biasing member 24 urges lower collar 20 upwardly into a lower end of upper collar 18 to move the upper collar 18 to its extended or high profile position. See FIGS. 4 and 5. As discussed above, when upper collar 18 is in its extended position, abutment surface 55 is engaged with a top surface of guide ribs 37. It is also noted that when the upper collar 18 is in its extended position, the upper end 40a of rib 40 engages the lower end of angled protrusions 36 of upper collar 18.

Figure 7:
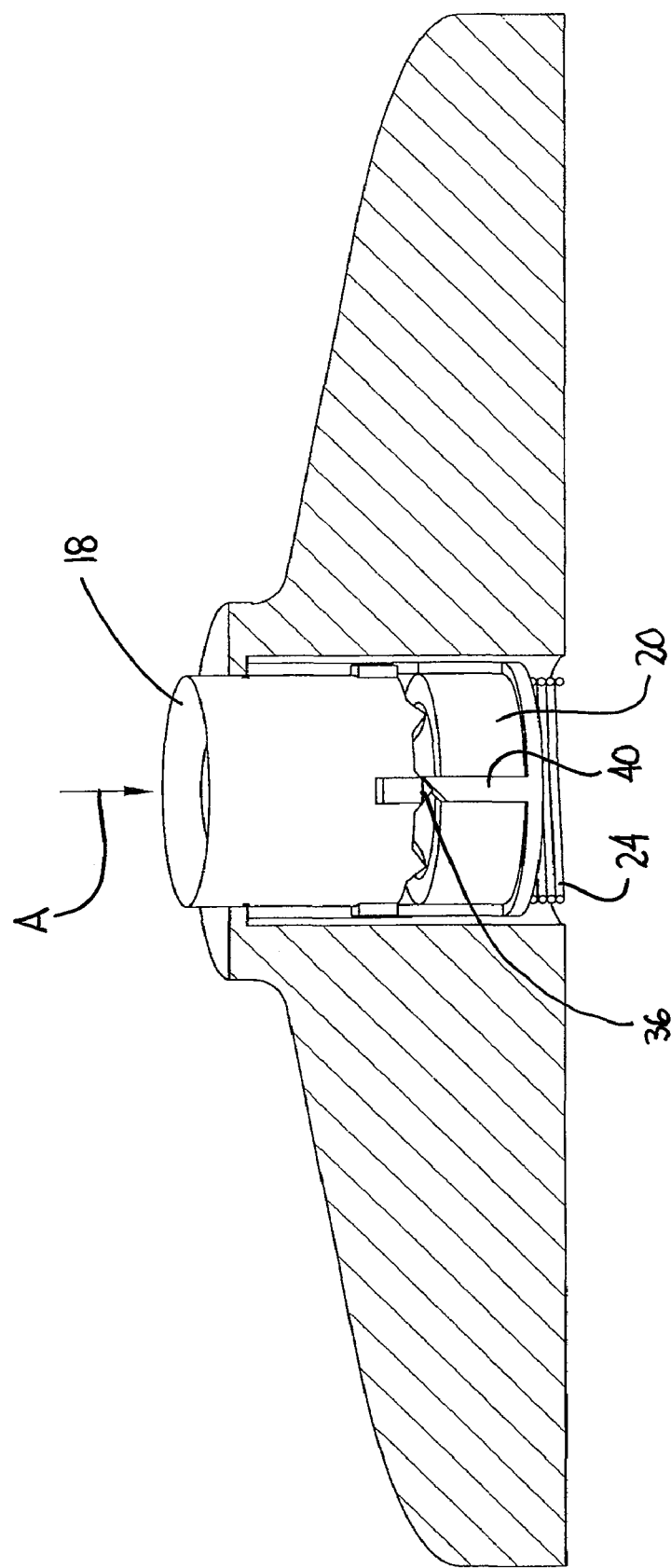
FIG. 7 is a partial cross-sectional view of the access device shown in FIG. 6 as the septum is moved towards the retracted position.
Figure 8:
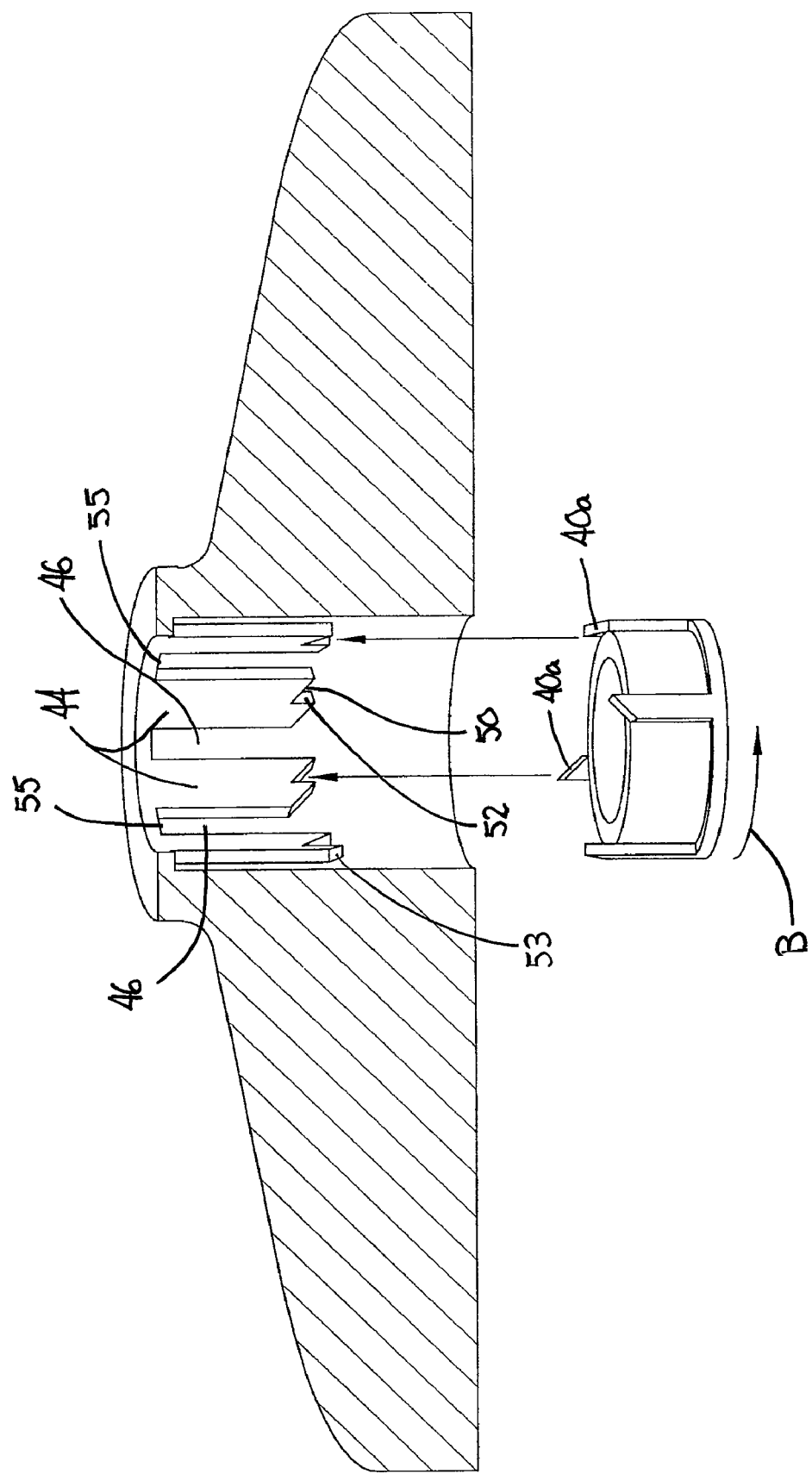
FIG. 8 is a side, partial cross-sectional view of the housing and lower collar of the access device shown in FIG. 7 with parts separated.

Referring to FIGS. 7-10, when upper collar 18 is pressed downwardly in the direction indicated by arrow "A" in FIG. 7, lower collar 20 is urged downwardly against biasing member 24 and angled protrusions 36 press against the top surface of ribs 40 to torque lower collar 20. When ribs 40 of lower collar 20 exit channels 46 of cam assembly 22, the torque applied by angled protrusions 36 on the upper end of ribs 40 rotates lower collar 20 in the direction indicated by arrow "B" in FIG. 8 causing the upper end 40a of ribs 40 to move into recessed surfaces 50 of retaining members 44 and abut against stop portion 52 of retaining members 44. When this occurs, lower collar 20 and, thus, upper collar 18 are retained in a retracted or low profile position. See FIGS. 9 and 10.

Figure 11:
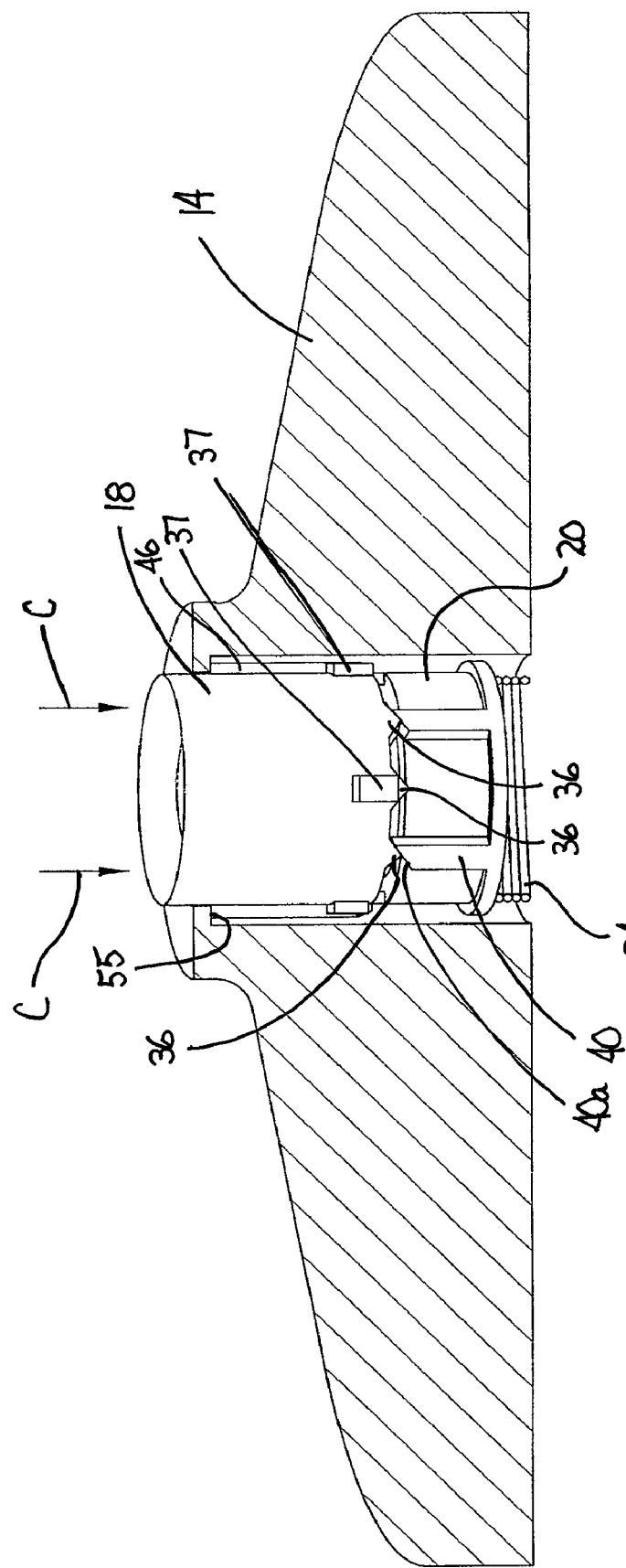
FIG. 11 is a side, partial cross-sectional view of the access device shown in FIG. 7 as the upper collar is pressed downwardly to return the septum to the extended position.
Figure 12:
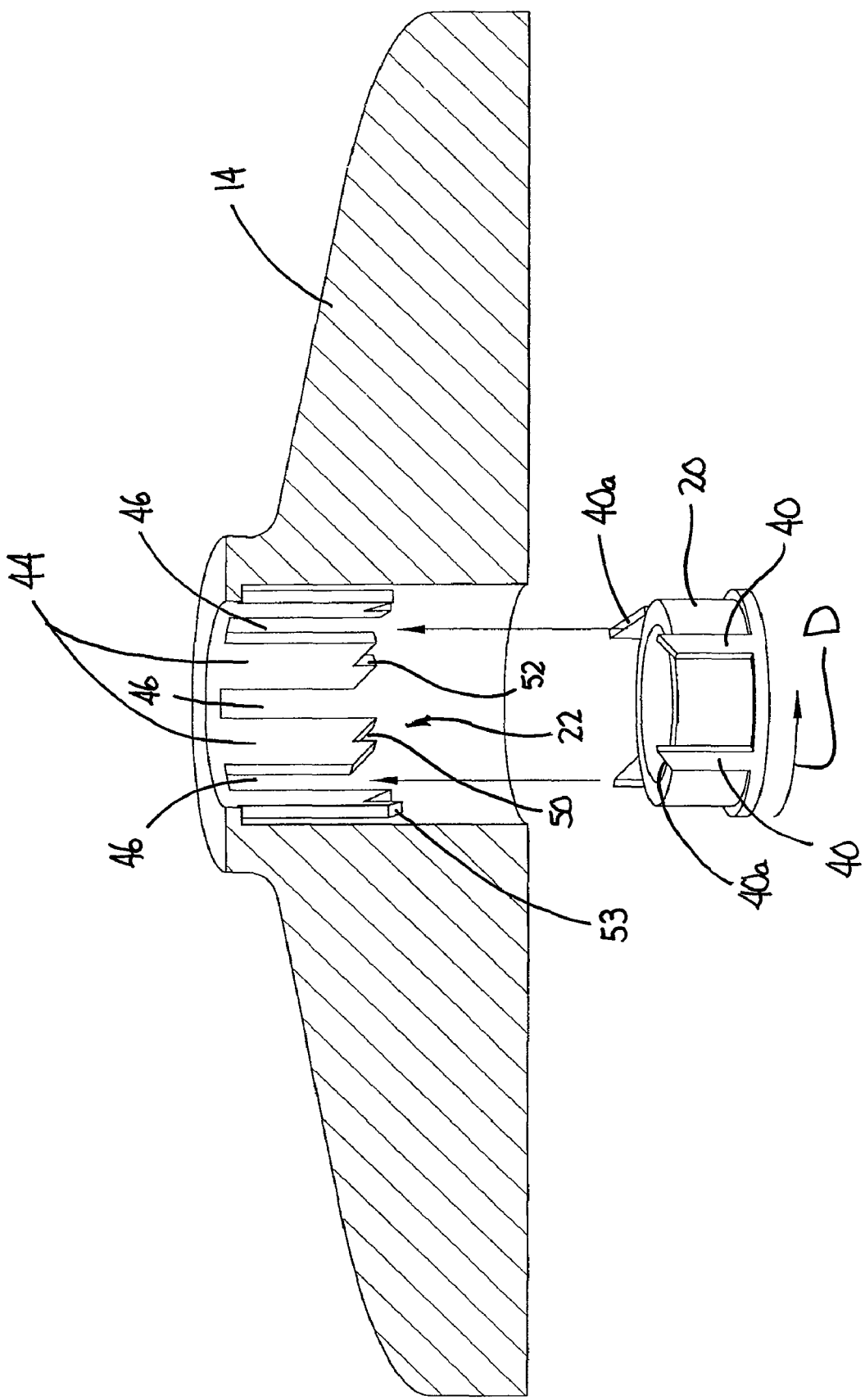
FIG. 12 is a side, partial cross-sectional view of the housing and lower collar of the access device shown in FIG. 11 with parts separated.

Referring to FIGS. 4, 5, 11 and 12, when upper collar 18 is in its retracted position and it is pressed downwardly in the direction indicated by arrows "C" in FIG. 11, the upper end 40a of rib 40 is moved downwardly and passes under stop portion 52 of cam assembly 22 (FIG. 12) and lower collar 18 rotates in the direction of arrow "D" in FIG. 12 as discussed above. When lower collar 20 rotates, ribs 40 once again align with channels 46 of cam assembly 22 and biasing member 24 urges lower collar 20 upwardly to move upper collar 18 and septum 26 to the extended position. It is noted that sloped guide surfaces 53 of retaining members 44 in combination with biasing member 24 guides ribs 40 into channels 46.

Figure 6:
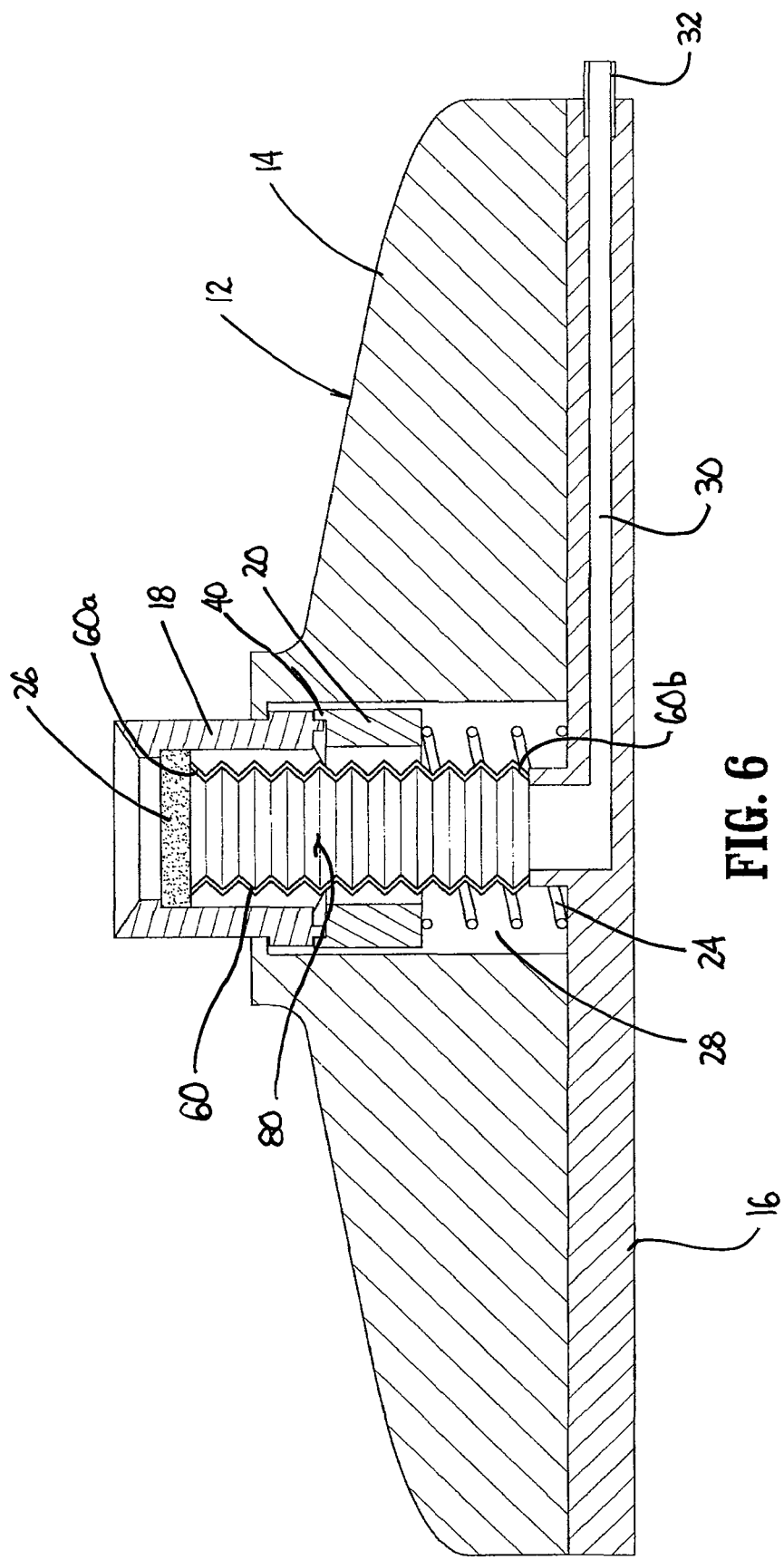
FIG. 6 is a cross-sectional view of the access device shown in FIG. 1 with the septum in an extended position.

Referring to FIGS. 3 and 6 and as discussed above, septum 26 is secured to an underside of upper collar 18. In one embodiment, a sleeve 60 has a first end 60a secured to a bottom surface of septum 26 and a second end 60b secured to lower body portion 16. Sleeve 60 provides a sealed passage 80 from septum 26 to outlet channel 30 of lower body portion 16. Sleeve 60 has an extendable configuration to facilitate movement of upper collar 18 to its extended position. In one embodiment, sleeve 60 has a flexible bellows-like construction. It is envisioned that other extendable sleeve configurations may be used. It is also envisioned that upper body portion 14 of housing 12 may have an o-ring or other sealing means to prevent the entry of substances found beneath the surface of the skin into cavity 28 along a path between upper collar 18 and a side wall of cavity 28.

In use, implantable access device 10 is implanted beneath the skin (FIG. 1) in a known manner with upper collar 18 in its retracted position. When medical personnel would like to inject or withdraw a fluid from device 10, the general area of skin near access device 10 can be pressed downwardly to press upper collar 18 into housing 12. As discussed above, when this occurs, rib 40 (FIG. 3) of lower collar 20 moves under stop portion 52 of cam assembly 22 and lower collar 20 is rotated to align ribs 40 of lower collar 20 with channels 46 of cam assembly 22. When this occurs, lower collar 20 and upper collar 18 are urged upwardly by biasing member 24 such that upper collar 18 and septum 26 move to the extended, high profile position. In this position, a top surface of upper collar 18 will press against an undersurface of the skin such that the location of septum 26 will be apparent to medical personnel. See FIG. 2. After a medical procedure has been performed, upper collar 18 can be returned to the retracted position in the manner discussed above by pressing downwardly on upper collar 18. Alternatively, it is envisioned that upper collar 18 may be pressed downwardly during a medical procedure, such as while inserting a needle through septum 26, to return the upper collar to the retracted position.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An implantable access device comprising:
   a housing defining a cavity and an outlet channel, the cavity being in fluid communication with the outlet channel;
   a pierceable septum sealingly enclosing an upper end of the cavity, the septum being movably supported in relation to the housing and being movable from a first, lower-profile position to a second, higher-profile position located externally of the cavity, wherein the implantable access device is dimensioned to be implanted beneath the skin of a patient and the septum is movable to the second, higher-profile position to enable medical personnel to identify the location of the access device beneath the skin; and
   a biasing member positioned to urge the septum towards the higher profile position.

2. The implantable access device according to claim 1, further including an upper collar positioned within the cavity and defining a throughbore, the septum being supported on the upper collar and sealing one end of the throughbore of the upper collar.

3. The implantable access device according to claim 2, wherein the upper collar is movable within the cavity from a first position to a second position to move the septum from the lower-profile position to the higher-profile position.

4. The implantable access device according to claim 3, further including a biasing member positioned to urge the upper collar from the first position to the second position.

5. The implantable access device according to claim 4, further including a lower collar rotatably supported within the cavity of the housing.

6. The implantable access device according to claim 5, wherein a lower end of the upper collar is positioned within the cavity to abut an upper end of the lower collar.

7. The implantable access device according to claim 6, wherein the lower end of the upper collar includes at least one angled protrusion and the upper end of the lower collar includes at least one rib, the at least one angled protrusion engaging the at least one rib to apply torque to the lower collar.

8. The implantable access device according to claim 7, further including a cam assembly defining at least one retaining member and at least one channel, wherein the rib of the lower collar and at least one guide rib of the upper collar are slidable within the at least one channel.

9. The implantable access device according to claim 8, wherein the cam assembly is fixedly secured within the housing such that the upper collar and the lower collar are rotatably fixed within the housing when the rib of the lower collar and the guide rib of the upper collar are positioned within the at least one channel.

10. The implantable access device according to claim 9, wherein when the upper collar is in the first position, the rib of the lower collar is pushed from the at least one channel and rotated by the angled protrusion, such that the rib engages the retaining member and the lower collar is retained in a lower portion of the cavity to retain the upper collar in the first position and retain the septum in the lower-profile position.

11. The implantable access device according to claim 10, wherein the at least one retaining member includes an angled recess and a stop member, the rib engaging the stop member when the septum is retained in the lower-profile position.

12. The implantable access device according to claim 11, wherein when the septum is in the lower-profile position, the upper collar can be pressed downwardly to urge the lower collar downwardly within the cavity to disengage the at least one rib of the lower collar from the stop member and allow the lower collar to rotate to realign the at least one rib with the at least one channel such that the biasing member moves the septum to the higher-profile position.

13. The implantable access device according to claim 1, further including an annular sleeve having a first end connected to a bottom surface of the septum and a second end connected to the housing, the sleeve defining a sealed flow path between the septum and the outlet channel.

14. The implantable access device according to claim 13, wherein the annular sleeve is in the form of a bellows-like member.

* * * * *